(12) United States Patent
Gatschet (10) Patent No.: US 12,256,859 B1
(45) Date of Patent: Mar. 25, 2025

(54) CONTACT FREE PASS THROUGH DELIVERY SYSTEM

(71) Applicant: Thomas J. Gatschet, Topeka, KS (US)

(72) Inventor: Thomas J. Gatschet, Topeka, KS (US)

( * ) Notice: Subject to any disclaimer, the term of this patent is extended or adjusted under 35 U.S.C. 154(b) by 214 days.

(21) Appl. No.: 17/676,791

(22) Filed: Feb. 21, 2022

Related U.S. Application Data (60) Provisional application No. 63/360,051, filed on Aug. 31, 2021.

(51) Int. Cl.
*A47G 29/14* (2006.01)
*A47G 29/30* (2006.01)
*A61L 2/10* (2006.01)

(52) U.S. Cl.
CPC ........... *A47G 29/141* (2013.01); *A47G 29/30* (2013.01); *A61L 2/10* (2013.01); *A47G 2029/147* (2013.01); *A61L 2202/11* (2013.01)

(58) Field of Classification Search
CPC ...... A47G 29/141; A47G 29/30; A47G 29/28; A47G 29/20; A47G 2029/142; A47G 2029/147; E06B 7/32; E05G 7/00; A61L 2/10; A61L 2202/11; G06Q 10/0836
See application file for complete search history.

(56) References Cited

U.S. PATENT DOCUMENTS

| | | | | |
|---|---|---|---|---|
| 5,774,053 A | * | 6/1998 | Porter | A47G 29/141 340/568.1 |
| 6,079,216 A | * | 6/2000 | de Marsillac Plunkett | A47G 29/20 312/286 |
| 6,204,763 B1 | * | 3/2001 | Sone | G06Q 10/087 340/5.1 |
| 6,415,552 B1 | * | 7/2002 | Khosropour | F25D 23/12 52/27 |
| 6,484,531 B1 | * | 11/2002 | Hambleton | F25D 23/10 312/286 |
| 9,700,168 B1 | | 7/2017 | Evans | |
| 10,238,210 B1 | * | 3/2019 | Shoenfeld | A47B 96/00 |
| 10,486,640 B2 | | 11/2019 | Ferguson et al. | |
| 10,820,733 B2 | | 11/2020 | Kaiserman et al. | |
| 10,954,068 B2 | * | 3/2021 | Nevison | G05B 15/02 |
| 11,478,099 B1 | * | 10/2022 | Bates | A47G 29/141 |
| 11,797,914 B2 | * | 10/2023 | Yamamoto | G06Q 10/0834 |

(Continued)

*Primary Examiner* — William L Miller
(74) *Attorney, Agent, or Firm* — Cramer Patent & Design PLLC; Aaron R. Cramer (57) ABSTRACT

A contact free pass through delivery system is a secure access system for package deliveries in a residential or commercial structure. It is intended to allow for delivery to an unattended location, non-contact deliveries, and to prevent package theft. The device is secured in an accessible exterior wall of a structure with doors that are accessed from outside the structure as well as another set inside. One or more of the secure compartments are refrigerated for delivery of food and other refrigerated items. One or more of the compartments are heated for delivery of warm meals. The remaining compartments would be available for delivery of parcels. All of the compartments are provided with an interlocked UV sanitizing system that kills germs, bacteria, and viruses, when both doors are closed. Additionally, all compartments are secured by a smart lock and camera system that is accessible via a local keypad and or a smart phone device from anywhere in the world to verify and allow deliveries.

18 Claims, 6 Drawing Sheets

(56) References Cited

U.S. PATENT DOCUMENTS

| | | | |
|---|---|---|---|
| 2001/0035703 A1 | 11/2001 | Scholefield | |
| 2001/0045449 A1* | 11/2001 | Shannon | G07C 9/21 232/19 |
| 2002/0035857 A1* | 3/2002 | Stein | A47G 29/141 70/277 |
| 2004/0263029 A1 | 12/2004 | Scholefield | |
| 2006/0179724 A1 | 8/2006 | Lee | |
| 2011/0130134 A1* | 6/2011 | Van Rysselberghe | G07F 7/00 455/422.1 |
| 2012/0158606 A1* | 6/2012 | Moudy | G06Q 10/083 705/332 |
| 2017/0213187 A1* | 7/2017 | Choi | H04N 7/181 |
| 2017/0286905 A1* | 10/2017 | Richardson | G06Q 10/0836 |
| 2018/0070753 A1* | 3/2018 | Eveloff | H04W 4/025 |
| 2018/0260777 A1 | 9/2018 | Judge | |
| 2019/0254459 A1* | 8/2019 | Hengst | A47G 29/141 |
| 2019/0262483 A1* | 8/2019 | Goidenko | A61L 2/0047 |
| 2020/0271358 A1* | 8/2020 | Oh | F25D 31/005 |
| 2021/0005033 A1* | 1/2021 | Roman | G06Q 10/0833 |
| 2021/0106160 A1* | 4/2021 | Janas | A47G 29/30 |
| 2021/0330830 A1* | 10/2021 | Zerello | A61L 2/10 |
| 2021/0338865 A1* | 11/2021 | Lee | A23L 3/001 |
| 2022/0012683 A1* | 1/2022 | Taylor | G07C 9/00182 |
| 2022/0028192 A1* | 1/2022 | O'Rourke | G07C 9/00182 |
| 2022/0039581 A1* | 2/2022 | Lee | A47G 29/30 |
| 2022/0058575 A1* | 2/2022 | Moudy | G07F 9/002 |
| 2022/0061572 A1* | 3/2022 | Snodgrass | G06Q 50/28 |
| 2022/0142388 A1* | 5/2022 | Foster | A47G 29/141 |
| 2022/0151419 A1* | 5/2022 | Lee | G06Q 10/083 |
| 2022/0155005 A1* | 5/2022 | Lee | G06Q 10/0832 |
| 2022/0339308 A1* | 10/2022 | Soderberg | A61L 2/28 |
| 2023/0153747 A1* | 5/2023 | Ruocco | G06Q 10/0836 232/31 |
| 2023/0309720 A1* | 10/2023 | Musilli | A61L 2/10 52/173.1 |
| 2024/0087386 A1* | 3/2024 | Asher | G06Q 10/0836 |
| 2024/0188698 A1* | 6/2024 | Johnson | A45C 11/20 |

\* cited by examiner

CONTACT FREE PASS THROUGH DELIVERY SYSTEM

RELATED APPLICATIONS

The present invention is a continuation of, was first described in, and claims the benefit of Provisional Application No. 63/360,051, filed Aug. 31, 2021, the entire disclosures of which are incorporated herein by reference.

FIELD OF THE INVENTION

The present invention relates generally to a contact free pass through delivery system.

BACKGROUND OF THE INVENTION

In the typical business day, millions of parcels and items are delivered around the world. While computerized tracking, customer databases, and electronic scanning has greatly increased productivity and reduced mistakes, one weak link remains the final delivery point, as large packages are often simply left on front porches of unattended residences and businesses. It is often simply not possible to be present when a package is delivered anymore, as many homes and buildings receive several packages a day.

Unfortunately, the criminal element is always present and such packages are often simply stolen. Package theft is an epidemic, and costs shippers, carriers, and customers several billion dollars annually. The same problems exist with food and meal delivery with the additional problem of keeping food cold and meals warm. Finally, pandemics such as COVID-19 have increased the need for contact free deliveries which an open door does not provide. Accordingly, there exists a need for a means by which parcels, food, and meals, can be safely and securely delivered to the intended recipient with reduced opportunity for theft and without the recipient being present. The development of the Contact Free Pass Through Delivery System fulfills this need.

SUMMARY OF THE INVENTION

In order to overcome the defects of the existing facilities, the invention provides a parcel and food delivery station that has an overall exterior enclosure adapted to protrude on an interior of a building structure, an exterior face including one or more compartments, each of the one or more compartments having an exterior insulated door, a hinge, a handle, and an access control means, an exterior door limit switch disposed on the exterior insulated door, an interior face allowing access to the one or more compartments via a respective interior insulated door, an interior door limit switch disposed on the respective interior insulated door, an interstitial space disposed between the overall exterior enclosure and the interior compartment. The interstitial space is filled with a plurality of thermal insulation, and a plurality of UV-C antibacterial lights energized for a first predetermined time period when the exterior door limit switch is initially closed and remain closed to sanitize one or more package deliveries or one or more food deliveries and the UV-C antibacterial lights are centrally disposed within the one or more compartments.

The overall exterior enclosure may be adapted to protrude on the exterior of the building structure. The overall exterior enclosure may be made of steel for strength, weather resistance and theft resistance. The one or more compartments may be one or more heated compartments. The one or more compartments may be one or more refrigerated compartments. The one or more compartments may be one or more storage compartments. The access control means may be accessed by a device selected from the group consisting of a keypad device, a smart phone interface device, or a bar code scanner device. The exterior face may be placed flush mounted to an exterior wall such that it is accessible to the one or more delivery personnel. The exterior face may be surface mounted to an exterior wall such that it is accessible to the one or more delivery personnel. Each of the one or more storage compartments may be insulated to prevent thermal transfer. The interior face may be disposed on a secure side of the exterior wall eliminating a need for the access control means. The exterior insulated door may be filled with the thermal insulation. The respective interior insulated door may be filled with the thermal insulation. The UV-C antibacterial lights may be energized for a second predetermined time period when the interior door limit switch is initially closed and remain closed. The UV-C antibacterial lights may be energized to sanitize one or more empty package containers or one or more empty food containers to ensure safe future use. The parcel and food delivery station may further comprise a video camera and a bar code reader adapted to allow one or more authorized users to verify the one or more package deliveries or the one or more food deliveries.

The parcel and food delivery station may securely access the one or more package deliveries or the one or more food deliveries within a residential structure. The residential structure may be selected from the group consisting of an apartment, a multifamily home, or a condominium. The parcel and food delivery station may securely access the one or more package deliveries or the one or more food deliveries within a commercial structure. The commercial structure may be selected from the group consisting of a business, an institutional establishment, or an industrial establishment.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 10 parcel and food delivery station
15 enclosure
20 exterior face
25 heated compartment
30 refrigerated compartment
35 storage compartment
40 exterior insulated door
45 hinge
50 handle
55 access control means
60 building structure
65 exterior wall
70 interior face
75 interior insulated door
80 interstitial space
85 interior compartment
90 thermal insulation
95 exterior door limit switch
100 interior door limit switch
105 UV-C antibacterial light
110 UV-C light rays
115 video camera
120 bar code reader
125 heating coils
130 refrigeration coils
135 refrigeration unit
140 AC power
145 power supply
150 main controller
155 Wi-Fi transmitter
160 cellular transmitter
165 temperature control unit

DESCRIPTION OF THE PREFERRED EMBODIMENTS

The best mode for carrying out the invention is presented in terms of its preferred embodiment, herein depicted within FIGS. 1 through 6. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Figure 1:
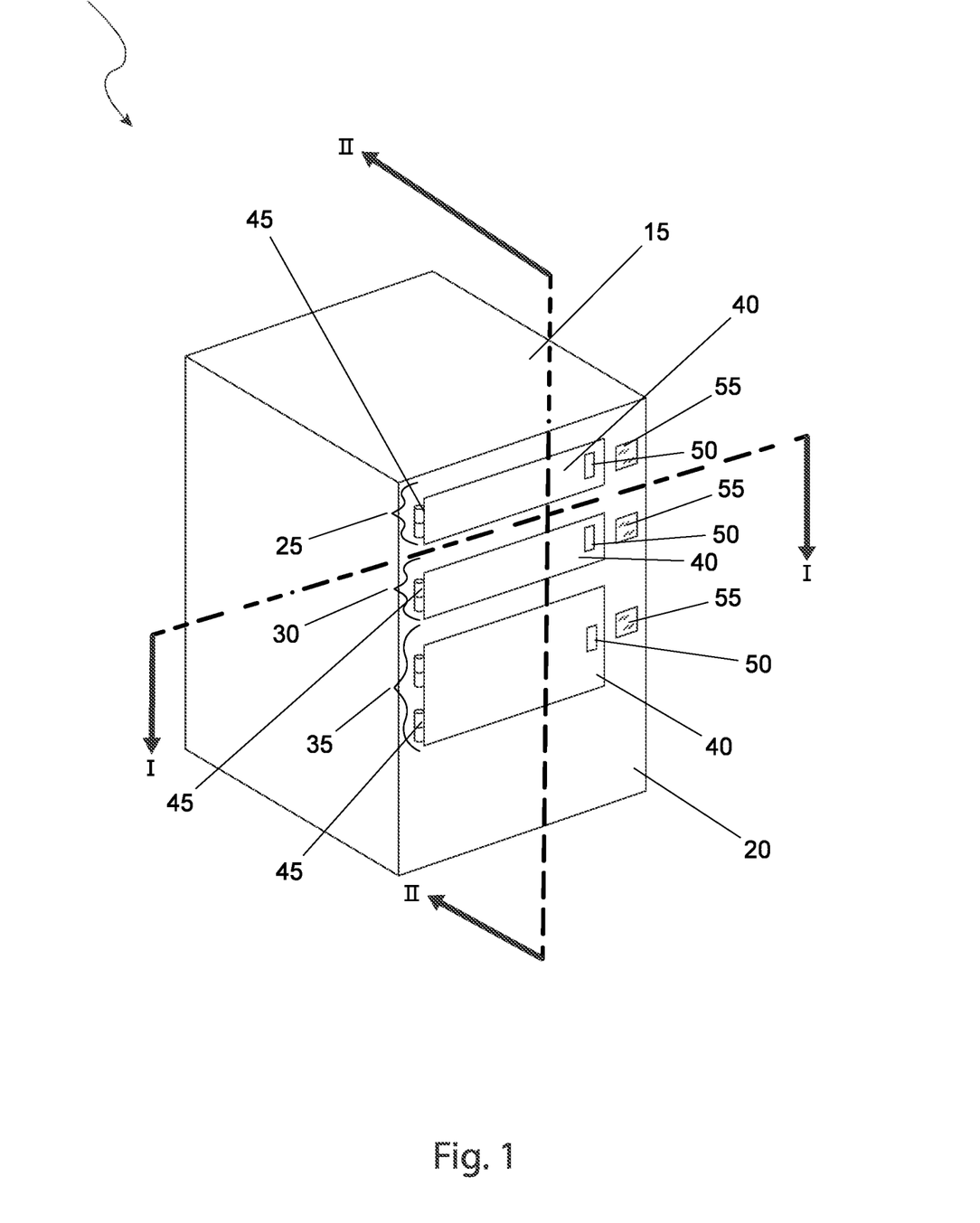
FIG. 1 is a perspective view of the parcel and food delivery station, according to the preferred embodiment of the present invention.

Referring now to FIG. 1, a perspective view of the parcel and food delivery station 10, according to the preferred embodiment of the present invention is disclosed. The parcel and food delivery station (herein also described as the "station") 10, provides for a secure access means for package and food deliveries in a residential or commercial structure 60. It is intended to allow for delivery to an unattended location, non-contact deliveries, and to prevent package theft. The invention is provided with an overall exterior enclosure 15 envisioned to be made of steel for strength, weather resistance and theft resistance. An exterior face 20 is provided with at least one (1) of the following: one (1) or more heated compartments 25, one (1) or more refrigerated compartments 30, and one (1) or more storage compartments 35. Each compartment 25, 30, 35 is provided with an exterior insulated door 40, a hinge 45, a handle 50, and an access control means 55. The access control means 55 may be accessed by a keypad, smart phone interface, a bar code scanner, or other method of electronic access. The exact method or methods of access is not intended to be a limiting factor of the present invention. The overall size of the exterior enclosure 15 as well as the heated compartments 25, the refrigerated compartments 30, and the storage compartments 35 will vary per individual need and installation. A station 10 installed on a small home or apartment will be generally the smallest, while one for a large home, business, commercial, or institutional establishment will be one of the largest. The exact size of the exterior enclosure 15 as well as the size and quantity of the heated compartments 25, the refrigerated compartments 30, and the storage compartments 35 is not intended to be a limiting factor of the present invention.

Figure 2:
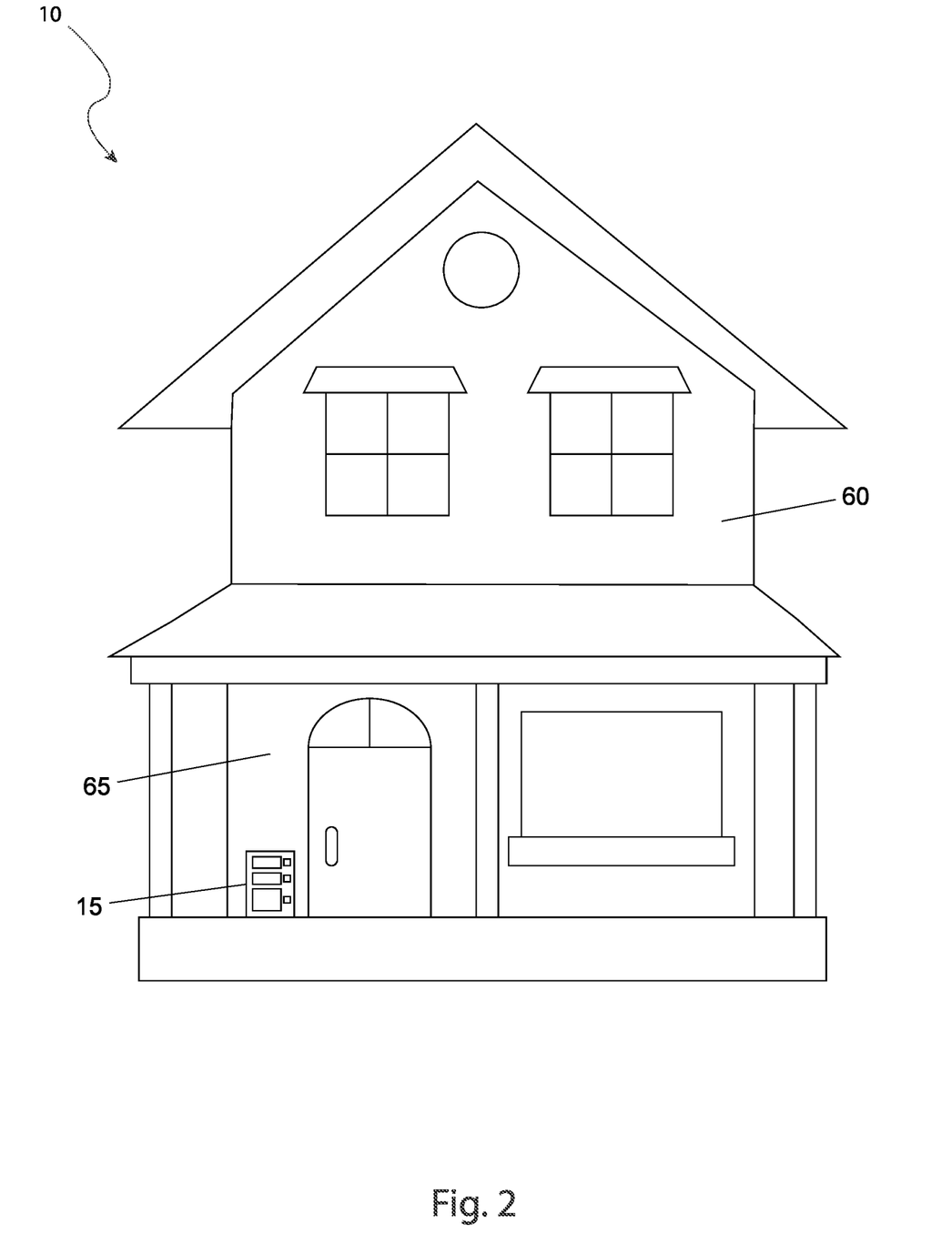
FIG. 2 is a perspective view of the parcel and food delivery station, in an installed state on the exterior of a building structure, according to the preferred embodiment of the present invention.

Referring next to FIG. 2, a perspective view of the station 10, in an installed state on the exterior of a building structure 60, according to the preferred embodiment of the present invention is depicted. The building structure 60 is represented by a single-family home for purposes of illustration in FIG. 2. However, other types of building structure 60 including but not limited to apartments, multifamily homes, condominiums, businesses, institutional establishments, and industrial establishments may utilize the features and benefits of the station 10. The depiction of a single-family home in FIG. 2 is not intended to be a limiting factor of the present invention. The exterior face 20 is placed either flush or surface mounted (herein depicted as flush-mounted for the purposes of illustration) in an exterior wall 65 such that it is accessible to delivery personnel.

Figure 3:
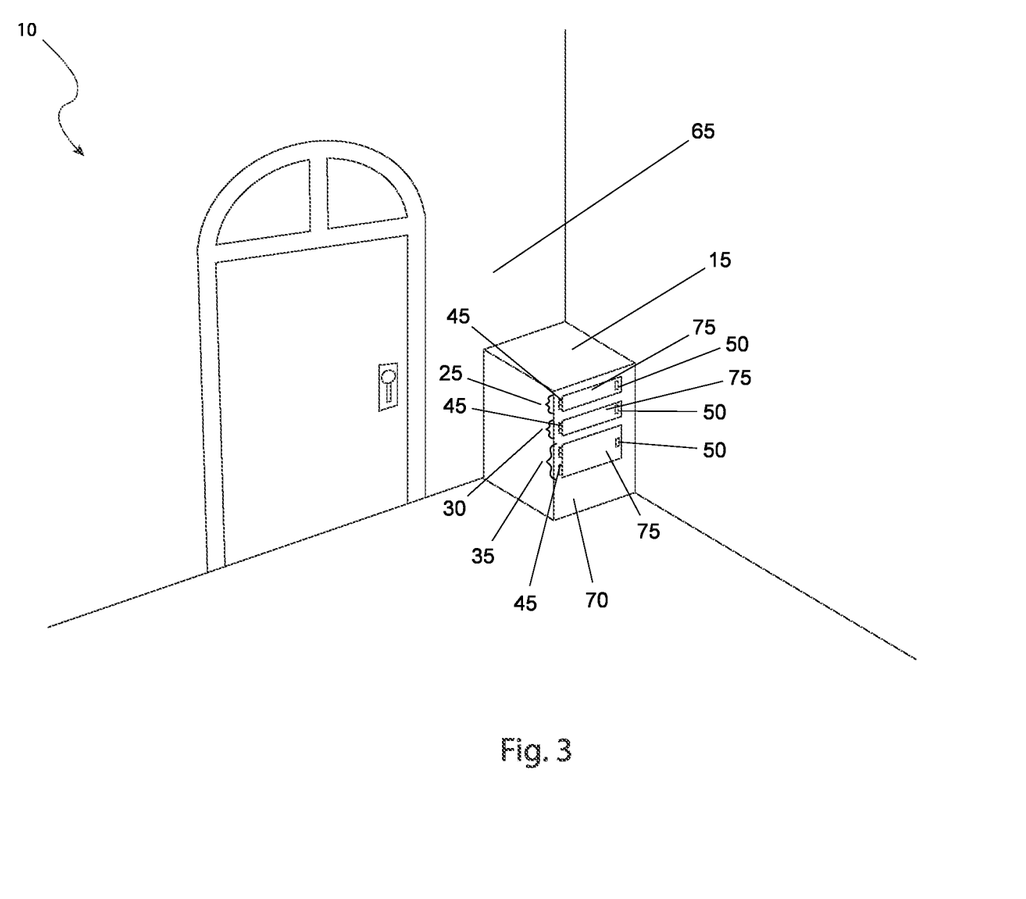
FIG. 3 is a perspective view of the parcel and food delivery station, in an installed state on the interior of a building structure, according to the preferred embodiment of the present invention.

Referring now to FIG. 3, a perspective view of the station 10, in an installed state on the interior of a building structure 60, according to the preferred embodiment of the present invention is shown. As before, the exterior enclosure 15 may protrude on the interior or the exterior of the building structure 60 (herein shown as protruding on the interior for purposes of illustration). The interior face 70 provides access to the heated compartments 25, the refrigerated compartments 30, and the storage compartments 35 via a respective interior insulated door 75. Each interior insulated door 75 is provided with a hinge 45 and handle 50. As the interior face 70 is envisioned to be on a secure side of the exterior wall 65, no need for an access control means 55 (as shown in FIG. 1) is required. It is envisioned that users may simply open the individual interior insulated door 75 in much the same manner as a standard kitchen cabinet door.

Figure 4:
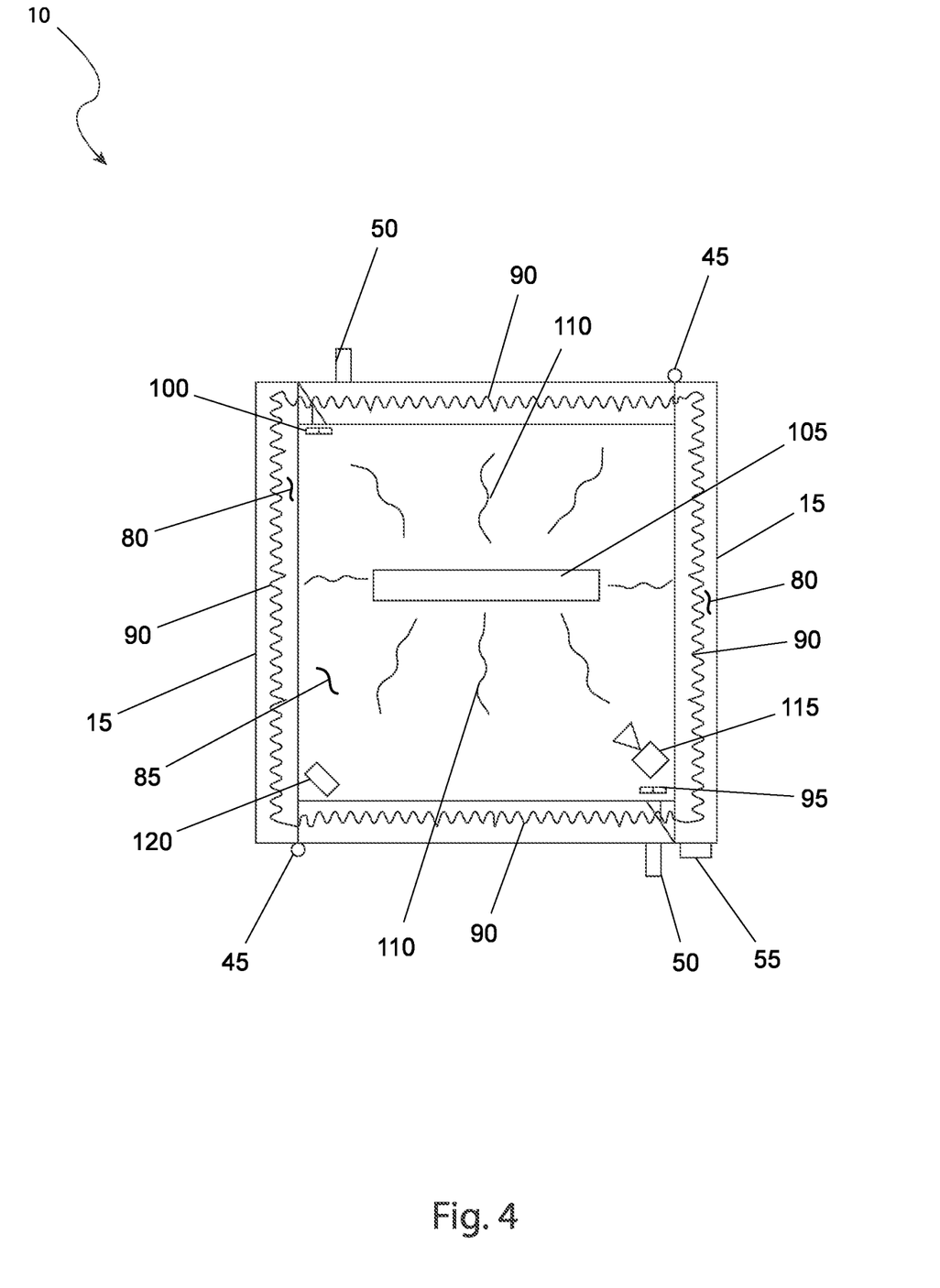
FIG. 4 is a sectional view of the parcel and food delivery station, as seen along a Line I-I, as shown in FIG. 1, according to the preferred embodiment of the present invention.

Referring next to FIG. 4, a sectional view of the station 10, as seen along a Line I-I, as shown in FIG. 1, according to the preferred embodiment of the present invention is disclosed. This view discloses the refrigerated compartments 30 as shown in FIG. 1, however, the interior components as depicted in FIG. 4 are identical for all heated compartments 25, all exterior face 20, and all storage compartments 35 as shown in FIG. 1. An interstitial space 80 between the exterior enclosure 15 and the interior compartment 85 is filled with thermal insulation 90. Thermal insulation 90 is also provided in the exterior insulated door 40 and the interior insulated door 75. The hinge 45 and the handle 50 is visible on both the exterior insulated door 40 and the interior insulated door 75 as well. An exterior door limit switch 95 is provided on the exterior insulated door 40, while an interior door limit switch 100 is provided on the interior insulated door 75. When both the exterior door limit switch 95 and/or the interior door limit switch 100 are initially closed, and remain closed, an UV-C antibacterial lights 105 is energized for a suitable time period. Such activation is thus initiated when a food product or parcel is placed inside the interior compartment 85, thus ensuring it is sanitized upon removing. Additionally, once removed, the UV-C antibacterial lights 105 will again initiate a sanitizing cycle of the empty interior compartment 85 to ensure safe future use. Such sanitation is provided by UV-C light rays 110. The interior of the interior compartment 85 is monitored by a video camera 115, as well as a bar code reader 120. The video camera 115 and the bar code reader 120 allow authorized users to verify placed food and/or parcels remotely on a conventional personal electronic device running a dedicated application associated with the station 10.

Figure 5:
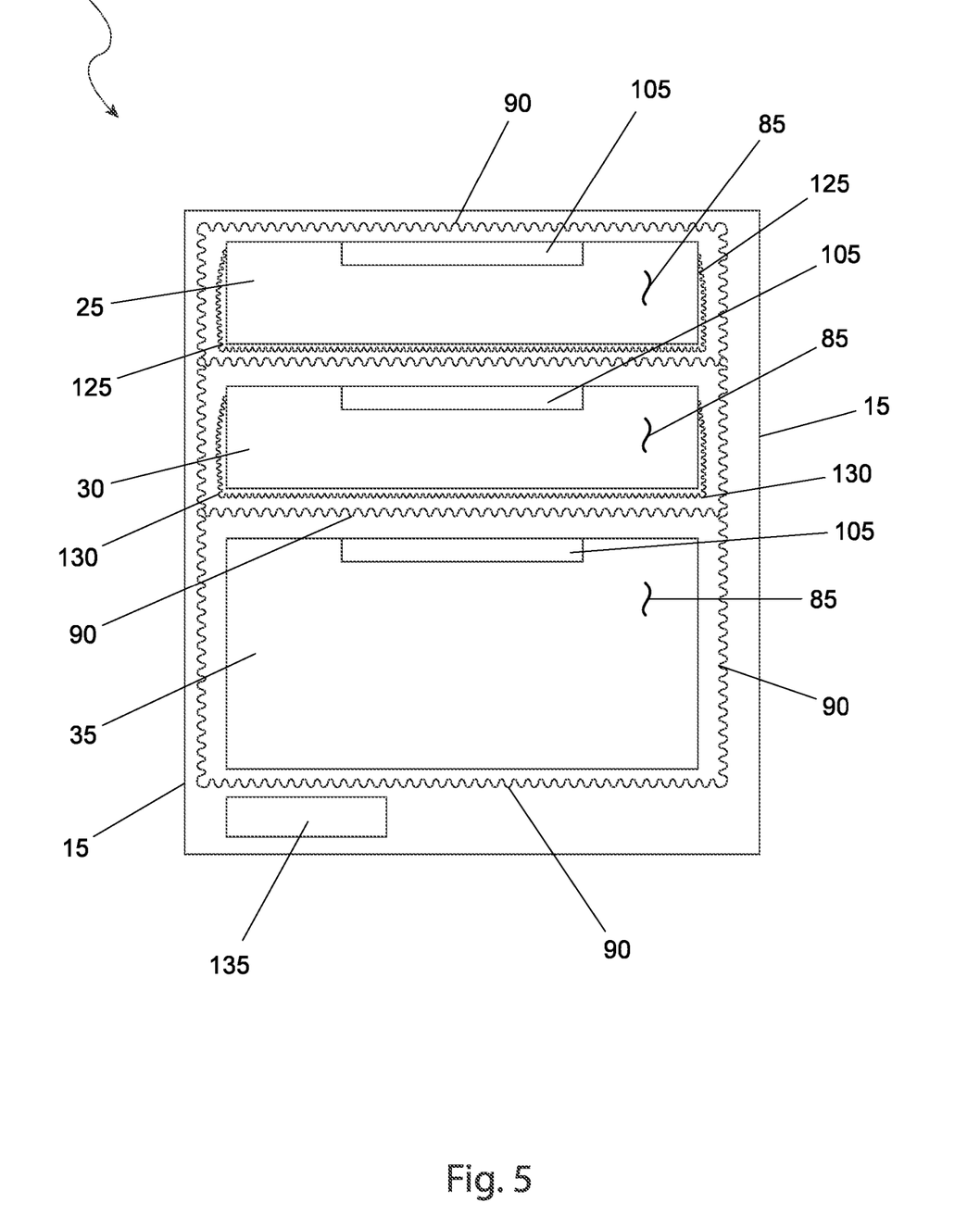
FIG. 5 is a sectional view of the parcel and food delivery station, as seen along a Line II-II, as shown in FIG. 1, according to the preferred embodiment of the present invention.

Referring now to FIG. 5, a sectional view of the station 10, as seen along a Line II-II, as shown in FIG. 1, according to the preferred embodiment of the present invention is depicted. This view clearly depicts the interior compartment 85 herein shown as the heated compartments 25, the refrigerated compartments 30, and the storage compartments 35 of the representative version as depicted in FIG. 1. Each interior compartment 85 is provided with a UV-C antibacterial lights 105, centrally located so as to adequately cover the interior compartment 85 with the UV-C light rays 110 (as shown in FIG. 4). The heated compartments 25 are provided with heating coils 125 for the purposes of keeping food such as fast food, pizza, chicken and the like hot. The refrigerated compartments 30 are provided with refrigeration coils 130 that operate in conjunction with a refrigeration unit 135 in the base of the exterior enclosure 15. Thermal insulation 90 is provided on all exterior facing elements of the exterior enclosure 15 as well as between each interior compartment 85 to prevent either warm or cold thermal transfer. Each storage compartment 35 is insulated as well to prevent thermal transfer between the exterior wall 65 (as shown in FIG. 2), as any other opening such as a door or window would be insulated as well.

Figure 6:
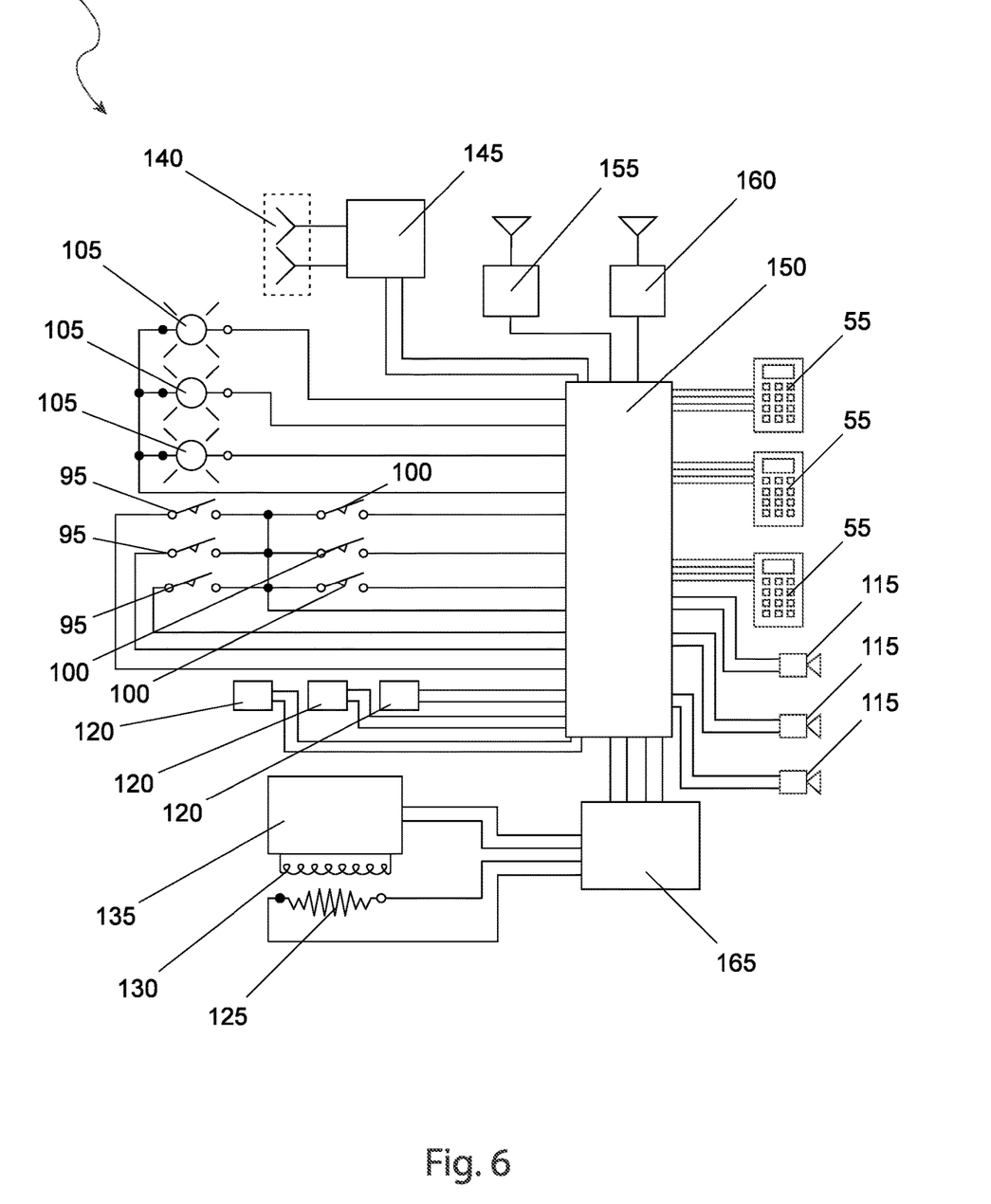
FIG. 6 is an electrical block diagram of the parcel and food delivery station, according to the preferred embodiment of the present invention.

Referring to FIG. 6, an electrical block diagram of the station 10, according to the preferred embodiment of the present invention is shown. AC power 140 enters into a power supply 145. Resultant power then is passed to a main controller 150. The exterior door limit switch 95 and the interior door limit switch 100 serve as inputs to the main controller 150 to notify authorized users of parcel or food placement into the station 10 as well as control of the UV-C antibacterial lights 105 as aforementioned described. Additional inputs are provided by the video camera 115, the bar code reader 120, and the access control means 55. The video camera 115 provides video observation of placement of any food and parcels. The bar code reader 120 provides the ability to read any 2D or 3D bar codes and relay such codes to the authorized user via their smart phone and associated app. The access control means 55 allows delivery personnel to enter a key code, previously supplied by the authorized user of the station 10 as part of delivery instructions, and also provided for package scanning via an integral code reader and access lock mechanism. Outputs from the main controller 150 include access to a Wi-Fi transmitter 155 and a cellular transmitter 160 to allow communication with the internet and thus the personal electronic device of the authorized user's smart phone. An additional output is provided to a temperature control unit 165 which controls the heating coils 125 as well as the refrigeration unit 135 which are connected to the refrigeration coils 130. The temperature control unit 165 may be controlled as to operation (energization) and temperature via settings on the user's personal electronic device.

2. Operation of the Preferred Embodiment

The preferred embodiment of the present invention can be utilized by the common user in a simple and effortless manner with little or no training. It is envisioned that the station 10 would be constructed in general accordance with FIG. 1 through FIG. 6. The user would procure the station 10 from conventional procurement channels such as appliance stores, home improvement stores, mechanical supply houses, mail order and internet supply houses and the like. Special attention would be paid to the overall physical size of the exterior enclosure 15, as well as the quantity and size of the heated compartments 25, the refrigerated compartments 30 and the storage compartments 35.

After procurement and prior to utilization, the station 10 would be installed in the following manner: a necessary rough opening would be made in the exterior wall 65 of the building structure 60. This rough opening would be framed and reinforced dependent on the construction of the exterior wall 65. Necessary flashing and caulking would be added as needed. The AC power 140 would be connected to the power supply 145. At this point in time, the station 10 is ready for utilization.

During utilization of the station 10, the following procedure would be initiated: upon approaching the station 10, delivery personnel would activate the appropriate heated compartments 25, the refrigerated compartments 30, or the storage compartments 35 dependent on the food or parcel being delivered; the access control means 55 would be accessed via a keypad, an application on the personal electronic device of the delivery personnel. Once opened, the food or parcel is placed in the respective interior compartment 85 and the exterior insulated door 40 closed. The access control means 55 then locks the exterior insulated door 40 keeping the parcel or food secure; upon closing the exterior insulated door 40, the respective UV-C antibacterial lights 105 energizes and sanitizes the food or parcel with UV-C light rays 110 for a predetermined time frame; the authorized user is notified of the delivery via the main controller 150 through the Wi-Fi transmitter 155 or the cellular transmitter 160; the delivered parcel or food item is removed from either the heated compartments 25, the refrigerated compartments 30 or the storage compartments 35 via opening of the respective interior insulated door 75; upon closing of the same interior insulated door 75 the UV-C antibacterial lights 105 is again activated for a predetermined period of time to sanitize the empty compartment 25, 30, 35 to allow for repeated use in a cyclical fashion.

The features of the station 10 provide the following benefits: security from outside threats, keeping foods from spoilage; allows for single use access and proof of delivery; complete control remotely for the owner; exposed surfaces of deliverables are sanitized prior to collection; reduction of possible identity theft opportunities; delivery of parcels and food in the authorized user's absence; meal deliveries that are kept warm until the authorized user is able to retrieve them; reduction of home intrusions; a refrigerated compartment for groceries; and sanitization of exposed surfaces on parcel or food.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A parcel and food delivery station, comprising:
   an overall exterior enclosure adapted to protrude on an interior of a building structure;
   an exterior face including one or more compartments, each of the one or more compartments having an exterior insulated door, a hinge, a handle, and an access control means;
   an exterior door limit switch disposed on the exterior insulated door;
   an interior face adapted to be in the interior of the building structure and allowing access to the one or more compartments via a respective interior insulated door;
   an interior door limit switch disposed on the respective interior insulated door;
   an interstitial space disposed between the overall exterior enclosure and the one or more compartments, the interstitial space is filled with a plurality of thermal insulation;
   a plurality of UV-C antibacterial lights energized for a first predetermined time period when the exterior door limit switch is initially closed and remains closed to sanitize one or more package deliveries or one or more food deliveries and the UV-C antibacterial lights are centrally disposed within the one or more compartments; and,
   wherein the UV-C antibacterial lights are energized for a second predetermined time period when the interior door limit switch is initially closed and remains closed.

2. The parcel and food delivery station, according to claim 1, wherein the overall exterior enclosure is adapted to protrude on the exterior of the building structure.

3. The parcel and food delivery station, according to claim 1, wherein the overall exterior enclosure is made of steel for strength, weather resistance and theft resistance.

4. The parcel and food delivery station, according to claim 1, wherein the one or more compartments are one or more heated compartments.

5. The parcel and food delivery station, according to claim 1, wherein the one or more compartments are one or more refrigerated compartments.

6. The parcel and food delivery station, according to claim 1, wherein the access control means is accessed by a device selected from the group consisting of a keypad device, a smart phone interface device, or a bar code scanner device.

7. The parcel and food delivery station, according to claim 1, wherein the exterior face is placed flush mounted to an exterior wall of the building structure such that it is accessible to the one or more delivery personnel.

8. The parcel and food delivery station, according to claim 1, wherein the exterior face is surface mounted to an exterior wall of the building structure such that it is accessible to the one or more delivery personnel.

9. The parcel and food delivery station, according to claim 1, wherein each of the one or more compartments are insulated to prevent thermal transfer.

10. The parcel and food delivery station, according to claim 1, wherein the interior face is disposed on a secure side of an exterior wall interior of the building structure.

11. The parcel and food delivery station, according to claim 1, wherein the exterior insulated door is filled with the thermal insulation.

12. The parcel and food delivery station, according to claim 1, wherein the respective interior insulated door is filled with the thermal insulation.

13. The parcel and food delivery station, according to claim 1, wherein the UV-C antibacterial lights are energized to sanitize one or more empty package containers or one or more empty food containers to ensure safe future use.

14. The parcel and food delivery station, according to claim 1, wherein the access control means comprises a video camera and a bar code reader adapted to allow one or more authorized users to verify the one or more package deliveries or the one or more food deliveries.

15. The parcel and food delivery station, according to claim 1, wherein the parcel and food delivery station securely accesses the one or more package deliveries or the one or more food deliveries within a residential said building structure.

16. The parcel and food delivery station, according to claim 15, wherein the residential building structure is selected from the group consisting of an apartment, a multifamily home, or a condominium.

17. The parcel and food delivery station, according to claim 1, wherein the parcel and food delivery station securely accesses the one or more package deliveries or the one or more food deliveries within a commercial said building structure.

18. The parcel and food delivery station, according to claim 17, wherein the commercial building structure is selected from the group consisting of a business, an institutional establishment, or an industrial establishment.

* * * * *